(12) United States Patent
Boday et al.

(10) Patent No.: US 9,271,498 B2
(45) Date of Patent: Mar. 1, 2016

(54) ANTIMICROBIAL PHT COATINGS

(71) Applicant: International Business Machines Corporation, Armonk, NY (US)

(72) Inventors: Dylan J. Boday, Tucson, AZ (US); Jeannette M. Garcia, San Jose, CA (US); James L. Hedrick, Pleasanton, CA (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/309,638

(22) Filed: Jun. 19, 2014

(65) Prior Publication Data

US 2015/0366202 A1 Dec. 24, 2015

(51) Int. Cl.
| | |
|---|---|
| *B05D 5/00* | (2006.01) |
| *A01N 43/64* | (2006.01) |
| *B05D 3/10* | (2006.01) |
| *C09D 5/16* | (2006.01) |

(52) U.S. Cl.
CPC .............. *A01N 43/64* (2013.01); *B05D 3/104* (2013.01); *B05D 3/107* (2013.01); *B05D 5/00* (2013.01); *C09D 5/16* (2013.01); *C09D 5/1693* (2013.01)

(58) Field of Classification Search
CPC ............ B05D 3/107; B05D 5/08; B05D 5/00; B05D 5/10; C09D 5/16; C09D 5/1606; C09D 5/1693
USPC .................................................. 427/337, 402
See application file for complete search history.

(56) References Cited

U.S. PATENT DOCUMENTS

| | | | |
|---|---|---|---|
| 2,889,277 | A | 6/1959 | Hughes |
| 3,340,232 | A | 9/1967 | Smith et al. |
| 3,598,748 | A | 8/1971 | Hirosawa |
| 3,957,742 | A | 5/1976 | Kveton |
| 4,106,904 | A | 8/1978 | Oude Alink et al. |
| 4,224,417 | A | 9/1980 | Hajek et al. |
| 4,225,481 | A | 9/1980 | Wagner |
| 4,246,160 | A | 1/1981 | Wagner et al. |
| 4,301,262 | A | 11/1981 | Wagner et al. |
| 4,877,451 | A | 10/1989 | Winnik et al. |

(Continued)

FOREIGN PATENT DOCUMENTS

| | | |
|---|---|---|
| CN | 101265255 A | 9/2008 |
| EP | 2636697 A1 | 9/2013 |

(Continued)

OTHER PUBLICATIONS

Henri Ulrich et al., Reaction of Chloromethyl Ether with Primary Amines, May 1961, pp. 1637-1638.

(Continued)

*Primary Examiner* — Kirsten Jolley
(74) *Attorney, Agent, or Firm* — Patterson & Sheridan, LLP

(57) ABSTRACT

Methods for making antimicrobial coating materials are described. Antimicrobial materials and antimicrobial material precursors are formed from hexahydrotriazine and/or a hemiaminal material and a non-fouling material and adhesive material may be incorporated into the antimicrobial materials and antimicrobial material precursors. The hexahydrotriazine and/or hemiaminal material may be made from a diamine and an aldehyde. Metal ions are also incorporated into the antimicrobial material precursors to form an antimicrobial material.

18 Claims, 2 Drawing Sheets

(56) References Cited

U.S. PATENT DOCUMENTS

| | | | |
|---|---|---|---|
| 5,112,796 | A | 5/1992 | Iannicelli |
| 5,674,377 | A | 10/1997 | Sullivan, III et al. |
| 5,830,243 | A | 11/1998 | Wolak et al. |
| 7,384,434 | B2 | 6/2008 | Malfer et al. |
| 2010/0107476 | A1 | 5/2010 | Cosimbescu |
| 2011/0070376 | A1* | 3/2011 | Wales et al. .................. 427/414 |
| 2012/0049308 | A1 | 3/2012 | Nishimura et al. |

FOREIGN PATENT DOCUMENTS

| | | |
|---|---|---|
| GB | 928112 A | 6/1963 |
| GB | 1531578 A | 11/1978 |
| WO | 0166614 A2 | 9/2001 |
| WO | 0198388 A1 | 12/2001 |
| WO | 0226849 A1 | 4/2002 |

OTHER PUBLICATIONS

Hemant S. Patel et al., Studies on Synthesis and Characterization of some Novel Aromatic Copolyesters based on s-Triazine, Iranian Polymer Journal, vol. 14, No. 12, 2005, pp. 1090-1098.

Fabian Suriano et al., Functionalized cyclic carbonates: from synthesis and metal-free catalyzed ring-opening polymerization to applications, Polymer Chemistry, The Royal Society of Chemistry, 2011, pp. 528-533.

Sung Ho Kim et al., Hydrogen bonding-enhanced micelle assemblies for drug delivery, Biomaterials, 2010, pp. 1-9.

Wang Yulan et al., Synthesis and Properties of Poly-1, 3, 5-Triazines, Polymer Communications, No. 2, 1984, pp. 117-123.

John Markoff, Error at IBM Lap Finds New Family of Materials, New York Times, May 15, 2014, 4 pages.

Jeanette M. Garcia et al., Recyclable, Strong Thermosets and Organogels via Paraformaldehyde Condensation with Diamines, Science AAAS, vol. 344, May 16, 2014, pp. 732-735.

D.R. Anderson et al., Thermally resistance polymers containing the s-triazine ring, Journal of Polymer Science Part A-1: Polymer Chemistry, vol. 4, Issue 7, pp. 1689-1702.

T. Okita, Filter method for the determination of trace quantities of amines, mercaptans, and organic sulphides in the atmosphere, Atmospheric Environment (1967), vol. 4, Issue 1, Jan. 1970, pp. 93-102.

Raquel Lebrero et al., Odor abatement in biotrickling filters: Effect of the EBRT on methyl mercaptan and hydrophobic VOCs removal, Bioresource Technology, Special Issue: Innovative Researches on Algal Biomass, vol. 109, Apr. 2012, pp. 38-45.

Elbert, et al. "Conjugate Addition Reactions Combined with Free-Radical Cross-Linking for the Design of Materials for Tissue Engineering," Biomacromolecules 2001, 2, 430-441; Published on Web Mar. 3, 2001.

Ferrar, "Reactions of Formaldehyde With Aromatic Amines," J. Appl. Chem, 14, 1964, 389-399.

Geng, et al., "Nanoindentation behavior of ultrathin polymeric films," Polymer 46 (2005) 11768-11772; Available online Oct. 19, 2005.

Hiller, et al., "Laser-engravable hexahydrotriazine polymer networks," Mat Res Innovat (2002) 6:179-184.

Oliver, et al. "Measurement of hardness and elastic modulus by; instrumented indentation: Advances in understanding and; refinements to methodology," J. Mater. Res., vol. 19, No. 1, Jan. 2004, 3-20.

Singh, et al., "Ultrasound mediated Green Synthesis of Hexa-hydro Triazines," J. Mater. Environ. Sci. 2 (4) (2011) 403-406.

Stafford, et al., "A buckling-based metrology for measuring; the elastic moduli of polymeric thin films," Nature Materials_3_Aug. 2004, 545-550;Published online: Jul. 11, 2004.

Ke, et al., "Role of non-covalent and covalent interactions in cargo loading capacity and stability of polymeric micelles," J. Control Release, Nov. 10, 2014, vol. 193, p. 9-26 (published online Jul. 15, 2014).

Victor W.L. Ng, et al., "Antimicrobial hydrogels: A new weapon in the arsenal against multidrug-resistant infections,"Advanced Drug Delivery Reviews; vol. 78, Nov. 30, 2014, pp. 46-62.

Ekinci et al., "Preparation, Characterization and H2O2 Selectivity of Hyperbranched Polyimides Containing Triazine", Journal of Polymer Research, 2005, pp. 205-210.

* cited by examiner

ANTIMICROBIAL PHT COATINGS

BACKGROUND

The present disclosure relates to antimicrobial coatings, and more specifically, to the use of hexahydrotriazine and hemiaminal molecules, oligomers, and polymers derived from aromatic, aliphatic, and/or polyether diamines to create surface coatings which exhibit antimicrobial and non-fouling characteristics.

Polymer-supported metal ions for use as antimicrobials in consumer products are of current interest for the control of bacterial growth on surfaces. The use of silver as an antimicrobial dates back centuries, when solutions of silver salts were commonly consumed for the treatment of illness. Although silver ions generally exhibit bactericidal properties against various microorganisms, silver treatments can also cause apoptosis and necrosis of mammalian cells. Recently, there have been advances towards the use of silver ions and silver nanoparticles (AgNPs) in hydrogels for wound treatment, and thus, efforts have been made to modulate toxicity. The antimicrobial activity of silver and other metal salts has been attributed to the metal cation causing cell membrane disruption and subsequent lysis. Antimicrobial applications for metal-containing hydrogels are promising, however, metal ion incorporation into hydrogels, hydrogel surface adhesion, and bioadhesion fouling remain problematic.

Thus, what is needed in the art are improved antimicrobial surface coatings.

SUMMARY

In one embodiment, a method of preparing an antimicrobial material is provided. The method includes preparing an antimicrobial material precursor which includes an anti-fouling material and an adhesive agent. The antimicrobial material precursor may be disposed on a substrate and the antimicrobial material precursor may be exposed to metal ions to form an antimicrobial material.

In another embodiment, a method of preparing an antimicrobial material is provided. The method includes preparing an antimicrobial material precursor comprising an anti-fouling material. An adhesive agent layer may be disposed on the surface of a substrate and the antimicrobial material precursor may be disposed on the adhesive agent layer. The antimicrobial material precursor may be exposed to metal ions to form an antimicrobial material.

In yet another embodiment, a method comprising or preparing an antimicrobial material is provided. The method includes preparing an antimicrobial material precursor comprising an anti-fouling material. The antimicrobial material precursor includes an HT material having a plurality of trivalent hexahydrotriazine groups having the structure

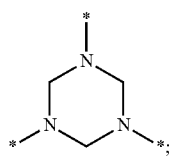

and
a plurality of divalent bridging groups having the structure

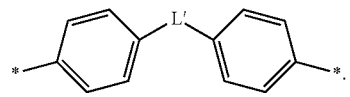

Each divalent bridging group may be bonded to two of the trivalent hexahydrotriazine groups, wherein L' is a divalent linking group. The antimicrobial material precursor may be disposed on the surface of a substrate and exposed to silver and/or copper ions to form an antimicrobial material.

DETAILED DESCRIPTION

Hexahydrotriazine (HT) materials and hemiaminal (HA) materials derived from aromatic, aliphatic, and/or polyether diamines may be used as a platform for creating antimicrobial materials and material precursors. Various metals, adhesive agents, and anti-fouling materials may be incorporated into the HA and HT materials. The antimicrobial materials and precursors may be single molecule species, oligomers, and/or polymers (i.e., polyhexahydrotriazine, PHT, polyhemiaminal, PHA). The anitmicrobial material precursors may be made using an aromatic diamine, an aliphatic diamine, a polyether diamine, or a mixture thereof to react with a formaldehyde (i.e. formaldehyde or paraformaldehyde). Such antimicrobial material precursors will form a complex with metal ions (i.e. silver ions and/or copper ions), partially or completely sequestering the metal within the antimicrobial material precursors to form the antimicrobial materials. The antimicrobial materials and precursors may also be reacted with various adhesive agents (i.e. dopamine) and anti-fouling materials (i.e. polyethylene glycol, PEG) to provide improved materials with antimicrobial properties.

Figure 1:
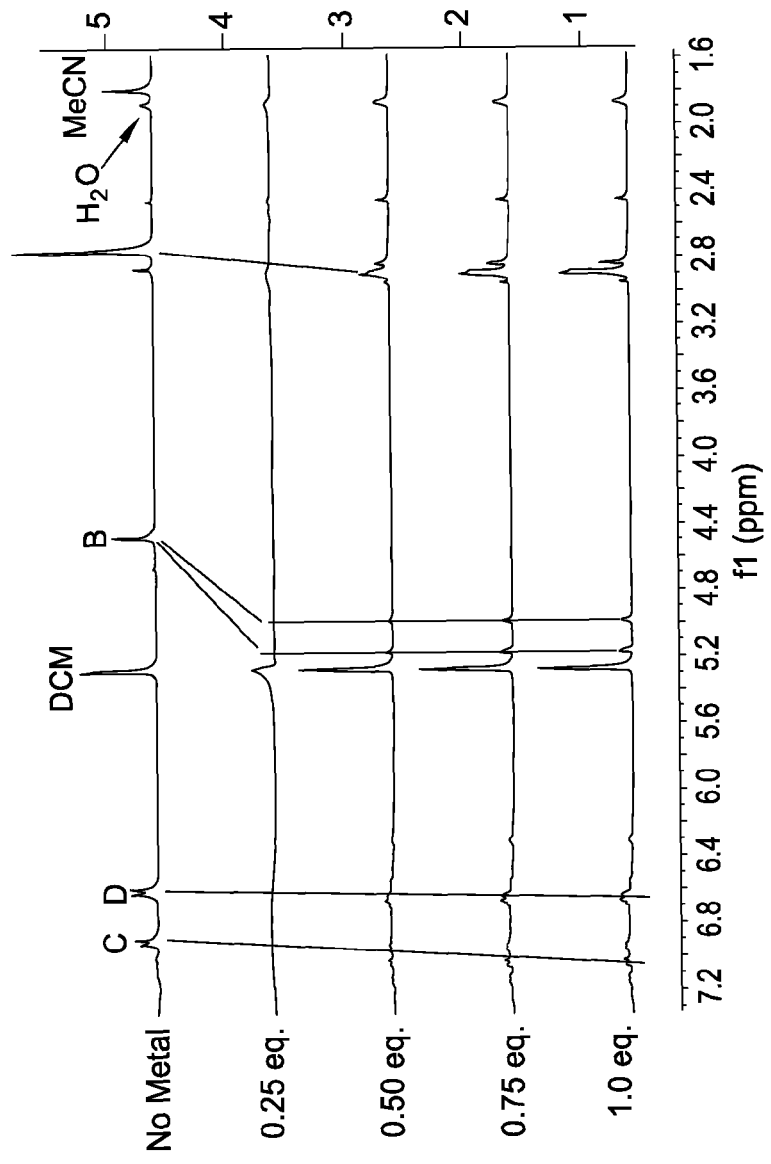
FIG. 1 illustrates an NMR spectrograph of an antimicrobial material before and after exposure to metal according to one embodiment.
Figure 1:
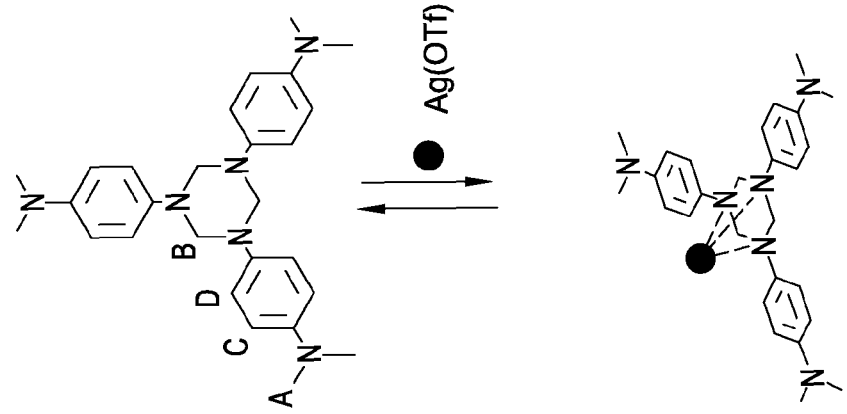

FIG. 1 is a 1H NMR spectrograph of an exemplary antimicrobial material precursor before and after exposure to metal ions according to one embodiment. The NMR spectra of the antimicrobial material precursor before exposure to metal ions is depicted in the "No Metal" spectrum, and the NMR spectra of the same material after exposure to metal ions is depicted at various molar equivalents (i.e. 0.25 eq, 0.50 eq, 0.75 eq, and 1.0 eq). In one embodiment, the antimicrobial material precursors may be considered antimicrobial materials after exposure to the metal ions. However, it is contemplated that the antimicrobial material precursors may exhibit antimicrobial properties independently of metal ion incorporation FIG. 1 is representative of the effect of various metals on various different kinds of HT and HA materials. As metal dosing of the HT or HA material increases, a peak shift and split (labeled "B") correlating to metal ion association with the antimicrobial material precursor may be observed. The original peak at approximately 4.4 ppm is non-existent after exposure to metal ions, indicating the reaction between the HT material and/or HA material is quantitative. Thus, the NMR spectrograph indicates metal is being sequestered and bound by the antimicrobial material precursor. In the embodiment of FIG. 1, the effect of exposing an HT material (small molecule analog of PHT material) to a solution of silver trifluoromethanesulfonate (also known as "triflate") in 80% by volume dichloromethane (DCM) and 20% by volume acetonitrile is shown. The shift of peak B is indicative of complexing between the HT material and silver ions.

Figure 2:
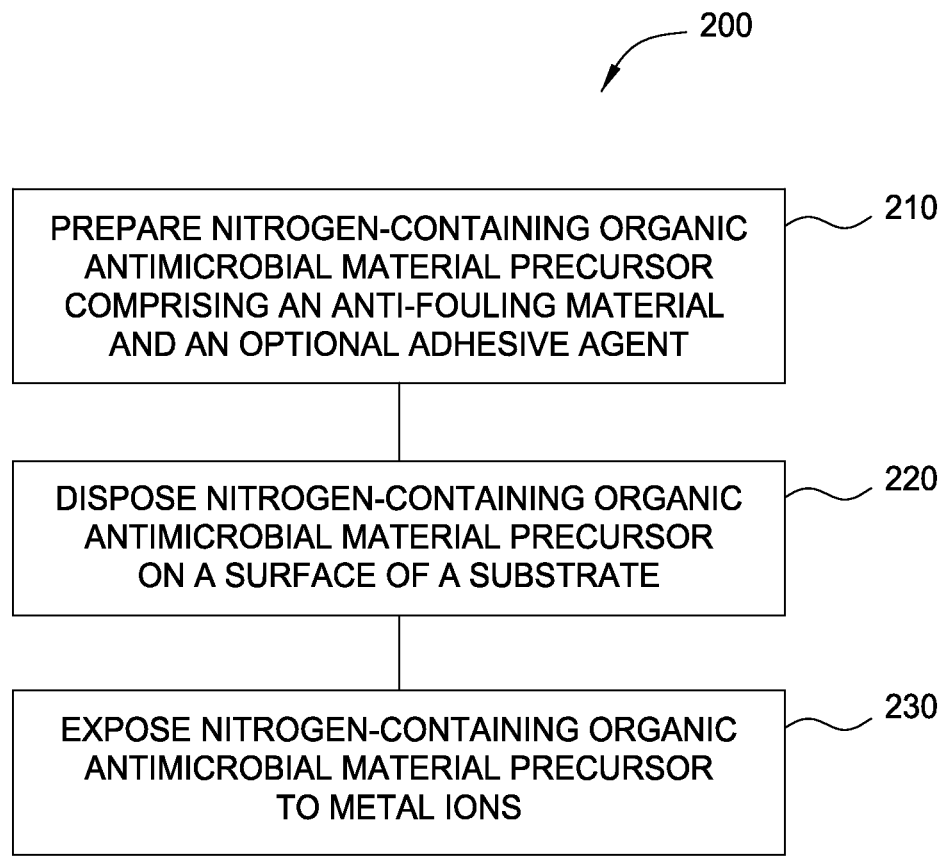
FIG. 2 is a flow diagram summarizing a method of forming an antimicrobial material according to one embodiment.

FIG. 2 is a flow diagram summarizing a method 200 of forming an antimicrobial surface coating according to one embodiment. The method 200 involves using a nitrogen-containing organic material (antimicrobial material precursor) having anti-fouling properties to sequester metals which exhibit antimicrobial activity. At operation 210, a nitrogen-containing organic antimicrobial material precursor comprising an anti-fouling material and an optional adhesive agent is prepared. The antimicrobial material precursor may include an HT material or an HA material, or both. The antimicrobial material precursor may be any of the antimicrobial material precursors described herein, single molecule species, oligomer species, and/or polymer species, and may be structured according to any morphology convenient for forming an antimicrobial surface coating. For example, the antimicrobial material precursor may be formed into particles, pellets, granules, powder, fibers, sheets, films, coatings or any other convenient form.

In one example, a diamine precursor, such as 4,4'-oxydianiline (ODA), may be reacted with a formaldehyde (i.e. paraformaldehyde and subsequently cured to enhance covalent cross-linking of the antimicrobial material precursor via condensation reactions. In one embodiment, the curing of the antimicrobial material precursor may be performed by heating the antimicrobial material precursor to between about 50° C. and about 280° C., such as greater than about 180° C., for example, about 200° C.

In one embodiment, an anti-fouling material is incorporated into the antimicrobial material precursor. The anti-fouling material may generally exhibit properties which prevent bioadhesion, and more specifically, prevent adhesion of proteins to a surface of a material. In one embodiment, the anti-fouling material may be an aliphatic compound. For example, a monofunctional or difunctional polyethylene glycol (PEG) oligomer may be utilized as the anti-fouling materials and may be incorporated into the antimicrobial material precursor. The antimicrobial material precursor incorporating the anti-fouling materials may exhibit antimicrobial characteristics in certain embodiments. In this example, a diblock copolymer of thiol-functionalized PEG may co-condense with the HT or HA material to form the antimicrobial material precursor with the integrated anti-fouling material. The anti-fouling material may comprise between about 2% and about 20%, such as about 5% of the antimicrobial material precursor by volume. In one embodiment, the anti-fouling material may be incorporated into the antimicrobial material precursor prior to performing the curing process. PEG generally exhibits a lower surface tension than the HT or HA material and the PEG anti-fouling material may gravitate toward a polymer/air interface after the antimicrobial material precursor is disposed on a substrate. As a result, the chemical incorporation of PEG greatly enhances the anti-fouling properties of the antimicrobial material precursor.

In addition to the anti-fouling material, an adhesive agent may be optionally utilized with the antimicrobial material precursor. The utilization of an adhesive agent is substrate dependent and takes into consideration the surface characteristics and desired application of a substrate. Generally, a substrate with a hydrophobic surface may utilize an adhesive material to couple the antimicrobial material precursor to the substrate. Utilization of an adhesive agent with a substrate having a hydrophilic surface may or may not be desired to couple the antimicrobial material precursor to the substrate. As such, the utilization of the adhesive agent is specific to the type and application of the desired substrate and may vary accordingly. However, it is believed that chemical incorporation of the adhesive agent may enhance the adhesive properties of the antimicrobial material precursor to the substrate.

In one embodiment, the adhesive agent may be incorporated into the antimicrobial material precursor prior to disposing the antimicrobial material precursor on a surface of a substrate at operation 220. Various adhesive agents that are capable of adhering the antimicrobial material precursor to the substrate may be utilized. In one example, a monomer, such as dopamine, may be utilized as the adhesive agent. In this example, the dopamine may be incorporated into the antimicrobial material precursor via a conjugate addition as a result of covalent bonding to amines in the HT or HA material. After incorporation of the adhesive agent, the antimicrobial material precursor may be disposed on the surface of the substrate at operation 220. The curing of the antimicrobial material precursor may be performed after the incorporation of the adhesive agent. It is believed that interaction between the amine moieties of the dopamine may bond to the substrate and function to adhere the antimicrobial material precursor to the substrate.

In another embodiment, the adhesive agent may be disposed on the surface of the substrate prior to disposing the antimicrobial material precursor on the substrate. In this embodiment, the adhesive agent, such as dopamine, may be deposited on the surface of the substrate to form an adhesive agent layer. For example, the dopamine may be homopolymerized on the surface of the substrate. At operation 220, the antimicrobial material precursor may then be disposed on the adhesive layer. Similar to the aforementioned embodiment, amines of the HT or HA material may undergo a conjugate addition with the amine moieties of the dopamine to adhere the antimicrobial material precursor to the substrate.

Thus, at operation 220, the antimicrobial material precursor may be disposed on the substrate. The antimicrobial material precursor may be disposed on the substrate in any convenient way. The antimicrobial material precursor may be disposed on the substrate by various methods. For example, the antimicrobial material precursor may be flowed, poured, sprayed, spin applied, ribbon applied, or otherwise applied to the substrate. In some embodiments, the film may be coated onto and/or adhered onto the substrate. Examples of suitable substrates include all touch surfaces where, computer screens, keyboards, contact lenses, various fabrics and fibers, catheter tubes, and various other type of medical equipment, among others.

A thickness of the antimicrobial material precursor disposed on the substrate may vary depending on the desired use of the substrate. For example, a surgical mask may have the antimicrobial material precursor coated thereon to a thickness of between about 1 nm and about 10 nm. Various applications for use in a healthcare setting, for example, a catheter tube, may have the antimicrobial material precursor coated thereon to a thickness of between about 10 nm and about 1000 nm. The antimicrobial material precursor may also be applied in various industrial settings, such as to the hull of a ship, to a thickness of several millimeters or more.

At operation 230, the antimicrobial material precursor may be exposed to metal ions. Any metal ion which exhibits antimicrobial characteristics may be utilized. For example, the antimicrobial material precursor may be exposed to silver and/or copper ions, among others. Non-metal antimicrobial materials may also be incorporated into the antimicrobial material precursor to for the antimicrobial material. It is contemplated that a single type of metal ion or combinations of different metal ions may be utilized. After the antimicrobial material precursor is exposed to the metal ions, the antimicrobial material precursor may be considered an antimicrobial material in certain embodiments.

The antimicrobial material precursor may be exposed to a solution containing the metal ions. In one example, a solvent or biological pH containing metal ions may be provided to the antimicrobial material precursor. The solvent may be a polar solvent, such as acetonitrile, dichloromethane, or combinations thereof. In one embodiment, a solution of silver triflate in 80% by volume DCM and 20% by volume acetonitrile may be provided to the antimicrobial material precursor. The solvent may function to swell the antimicrobial material precursor which facilitates incorporation of the metal ions throughout the antimicrobial material precursor.

Without limitation to any specific mechanism, it is believed that metals cations ($M^{+p}$) in the solvent may associate with one or more nitrogen atoms in the antimicrobial material precursor (HT, PHT, HA, or PHA material) to produce a complex according to formula (1):

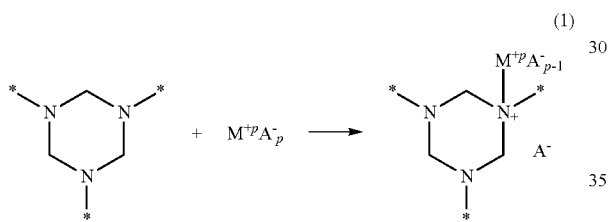

(1)

wherein $A^-$ is an anion. The metals are adsorbed onto the antimicrobial material precursor at a surface that contacts the solvent (See operation 230). The surface remains in contact with the solvent for a residence time selected to allow a desired amount of adsorption to occur. Typically, a residence time of 1 second to 60 minutes is used. The effective residence time may be less than the actual residence time if a portion of the antimicrobial material precursor has reached saturation.

In addition to embodiment utilizing a solvent to deliver the metal ions to the antimicrobial material precursor, various other methods may be employed. For example, chemical vapor deposition (CVD), atomic layer deposition (ALD), physical vapor deposition (PVD), and ion implantation processes may be utilized to provide the metal ions to the antimicrobial material precursor. It is contemplated that processing conditions and parameters utilizing the above referenced methods may facilitate interaction between the metal ions and the nitrogen atoms in the antimicrobial material precursor.

A PHT material suitable for forming an antimicrobial materials and antimicrobial material precursors as described herein is a molecule, oligomer, or polymer that has a plurality of trivalent hexahydrotriazine groups having the structure

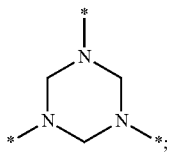

and
a plurality of divalent bridging groups of formula (2):

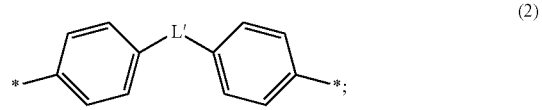

(2)

wherein L' is a divalent linking group selected from the group consisting of *—O—*, *—S—*, *—N(R')—*, *—N(H)—*, *—R"—*, and combinations thereof, wherein R' comprises at least 1 carbon and R" comprises at least one carbon, each starred bond of a given hexahydrotriazine group is covalently linked to a respective one of the divalent bridging groups, and each starred bond of a given bridging group is linked to a respective one of the hexahydrotriazine groups. In one embodiment, R' and R" are independently selected from the group consisting of methyl, ethyl, propyl, isopropyl, phenyl, and combinations thereof. Other L' groups include methylene (*—$CH_2$—*), isopropylidenyl (*—$C(Me)_2$-*), and fluorenylidenyl:

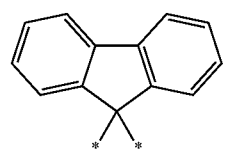

For PHT materials with bridging groups of formula (2), the HT may be represented by formula (3):

(3)

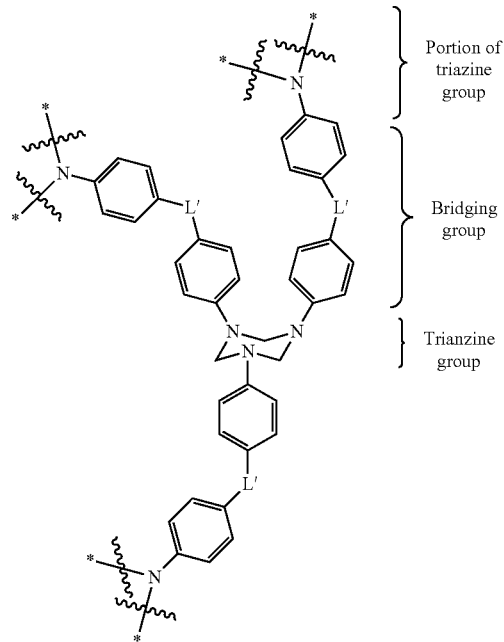

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (3) is a portion of a different hexahydrotriazine group.

The PHT may also be represented by the notation of formula (4):

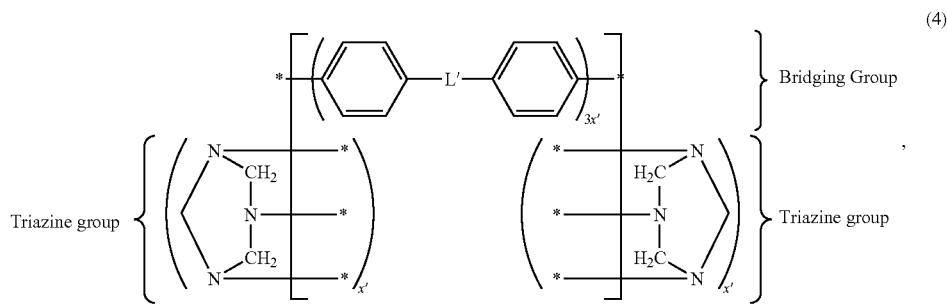

(4)

wherein x' is moles, L' is a divalent linking group selected from the group consisting of *—O—*, *—S—*, *—N(R')—*, *—N(H)—*, *—R"—*, and combinations thereof, wherein R' comprises at least 1 carbon and R" comprises at least one carbon. Each starred bond of a given hexahydrotriazine group of formula (4) is covalently linked to a respective one of the bridging groups. Additionally, each starred bond of a given bridging group of formula (2) is covalently linked to a respective one of the hexahydrotriazine groups. Polymer molecules may be capped or terminated by a capping group in place of a bridging group in formulas (3) and (4). Examples of capping groups include $CH_3$, hydrogen atoms, ether groups, thioether groups, and dimethyl amino groups.

The PHT or HT can be bound non-covalently to water and/or a solvent (e.g., by hydrogen bonds).

Exemplary non-limiting divalent bridging groups include:

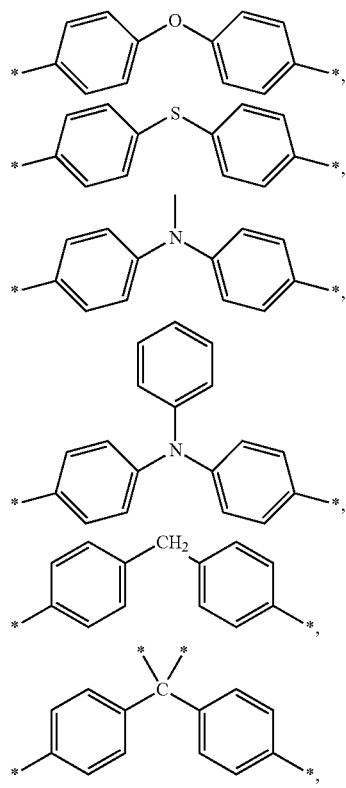

-continued

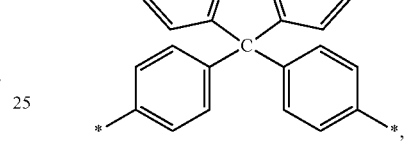

and combinations thereof.

A suitable PHT material may be made by forming a first mixture comprising i) one or more monomers comprising two aromatic primary amine groups, ii) an optional diluent monomer comprising one aromatic primary amine group, iii) paraformaldehyde, formaldehyde, and/or another suitable aldehyde, and iv) a solvent, and heating the first mixture at a temperature of about 50° C. to about 300° C., preferably about 165° C. to about 280° C., thereby forming a second mixture comprising a polyhexahydrotriazine. The heating time at any of the above temperatures can be for about 1 minute to about 24 hours. Diamine monomers suitable for making such PHT materials may have the general structure $H_2N$—Ar-L'-Ar-N—$H_2$, where Ar denotes a benzene ring group and L' is defined as described above. Diluent monomers suitable for including in the reaction are typically primary monoamines $RNH_2$, where the group R bonded to nitrogen has a structure according to formula (5), formula (6), formula (7), and/or formula (8):

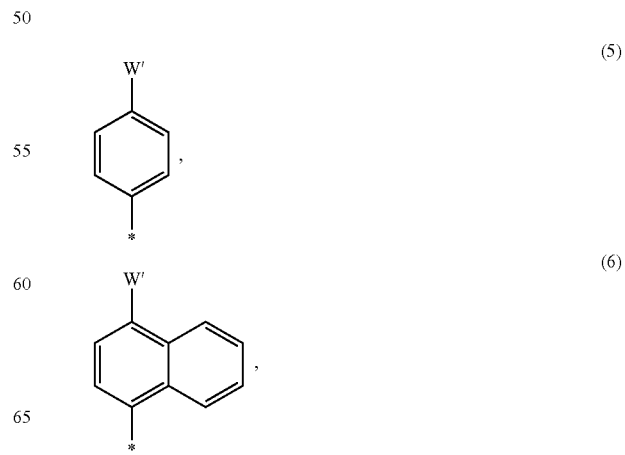

-continued

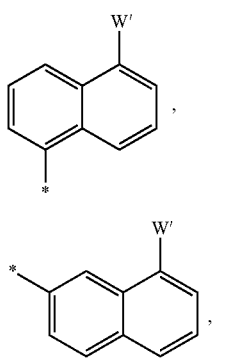

wherein W' is a monovalent radical selected from the group consisting of *—N(R$^1$)(R$^2$), *—OR$^3$, —SR$^4$, wherein R$^1$, R$^2$, R$^3$, and R$^4$ are independent monovalent radicals comprising at least 1 carbon. The starred bonds in formulas (5), (6), (7), and (8) denote bonds with the nitrogen atom of the primary amine monomer. Non-limiting exemplary diluent groups include:

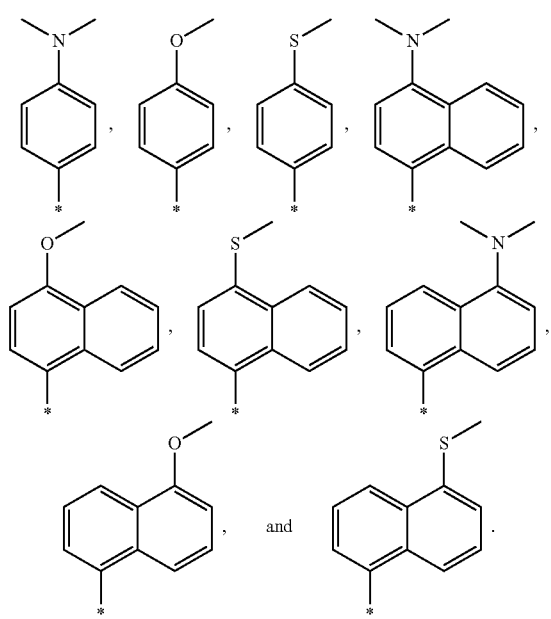

Diluent groups can be used singularly or in combination.

Non-limiting exemplary monomers comprising two primary aromatic amine groups include 4,4'-oxydianiline (ODA), 4,4'-methylenedianiline (MDA), 4,4'-(9-fluorenylidene)dianiline (FDA), p-phenylenediamine (PD), 1,5-diaminonaphthalene (15DAN), 1,4-diaminonaphthalene (14DAN), and benzidene, which have the following structures:

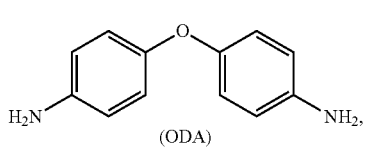
(ODA)

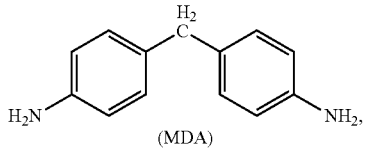
(MDA)

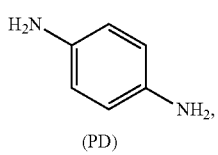
(FDA)

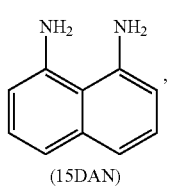
(PD)

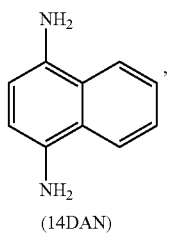
(15DAN)

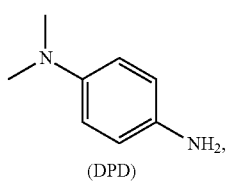
(14DAN)

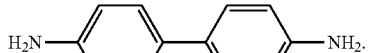
(benzidine)

Non-limiting exemplary diluent monomers include N,N-dimethyl-p-phenylenediamine (DPD), p-methoxyaniline (MOA), p-(methylthio)aniline (MTA), N,N-dimethyl-1,5-diaminonaphthalene (15DMN), N,N-dimethyl-1,4-diaminonaphthalene (14DMN), and N,N-dimethylbenzidene (DMB), which have the following structures:

(DPD)

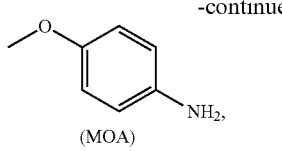
(MOA)

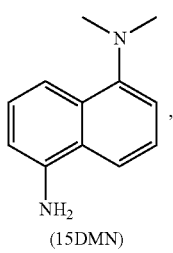
(MTA)

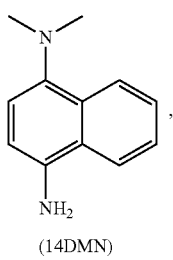
(15DMN)

(14DMN)

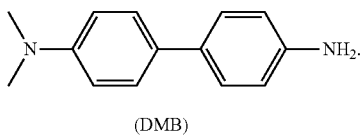
(DMB)

HT and HA antimicrobial material precursors may be used to incorporate metal ions to form an antimicrobial material surface coating. It should be noted that many diamines will react with aldehydes, such as formaldehyde, to form antimicrobial materials and antimicrobial material precursors. Other exemplary diamines include polyetherdiamines such as polyethylene glycol diamine. Alkyl diamines, such as hexane diamine, will also react with formaldehyde to form antimicrobial materials and antimicrobial material precursors. The polyether and alkyl derived materials might not readily form films, but gels, oligomers, and small molecules may be formed that are usable as antimicrobial materials and antimicrobial material precursors.

A related material that may be used to create an antimicrobial material or antimicrobial material precursor is a hemiaminal (HA) material. A polyhemiaminal (PHA) is a crosslinked polymer comprising i) a plurality of trivalent hemiaminal groups of formula (9):

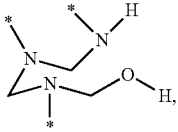

covalently linked to ii) a plurality of bridging groups of formula (10):

$$K'\text{—}(*)_{y'} \tag{10}$$

wherein y' is 2 or 3, and K' is a divalent or trivalent radical comprising at least one 6-carbon aromatic ring. In formulas (9) and (10), starred bonds represent attachment points to other portions of the chemical structure. Each starred bond of a given hemiaminal group is covalently linked to a respective one of the bridging groups. Additionally, each starred bond of a given bridging group is covalently linked to a respective one of the hemiaminal groups.

As an example, a polyhemiaminal can be represented by formula (11):

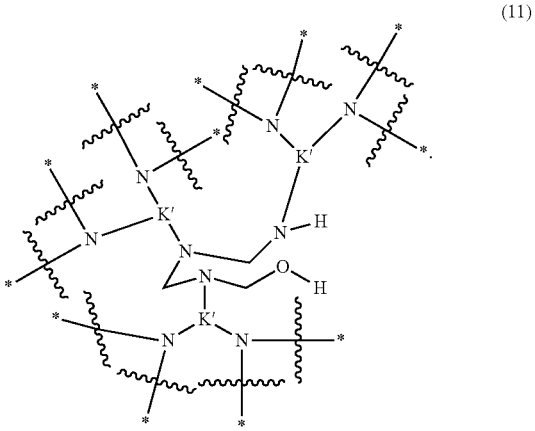

In this instance, each K' is a trivalent radical (y'=3) comprising at least one 6-carbon aromatic ring. It should be understood that each nitrogen having two starred wavy bonds in formula (11) is a portion of a different hemiaminal group.

The structure of formula (11) can also be represented using the notation of formula (12):

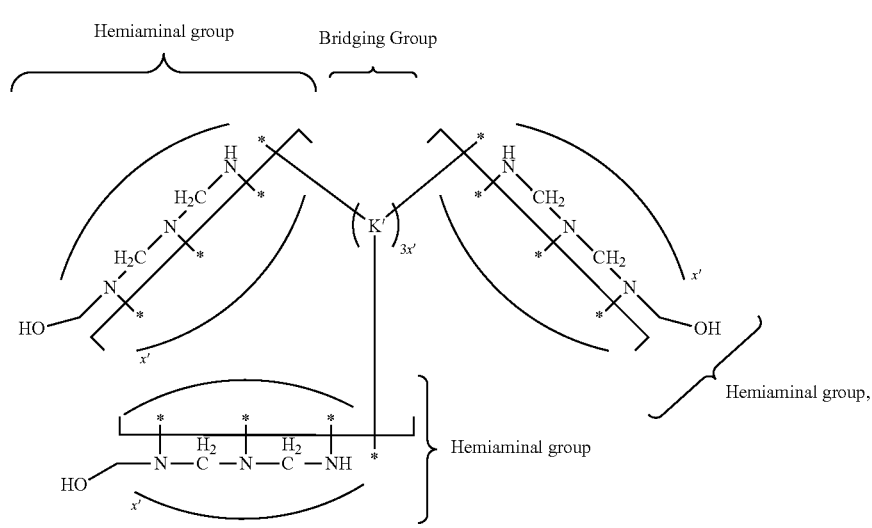

(12)

wherein x' is moles and each bridging group K' is a trivalent radical (y'=3 in formula (10)) comprising at least one 6-carbon aromatic ring. It should be understood that each starred nitrogen bond of a given hemiaminal group of formula (12) is covalently linked to a respective one of the bridging groups K'. Additionally, each starred bond of a given bridging group K' of formula (12) is covalently linked to a respective one of the hemiaminal groups.

Non-limiting exemplary trivalent bridging groups for HA materials include:

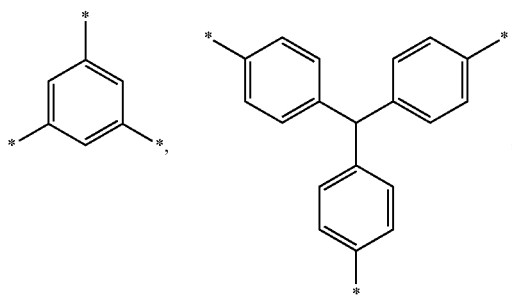

and

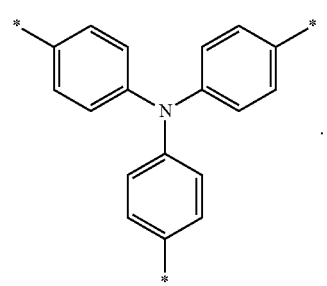

The bridging groups can be used singularly or in combination.

Polyhemiaminals composed of divalent bridging groups K' can be represented herein by formula (13):

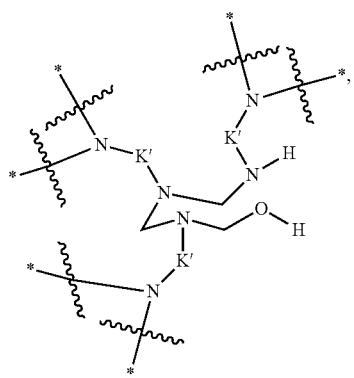

(13)

wherein K' is a divalent radical (y'=2 in formula (10)) comprising at least one 6-carbon aromatic ring. Each nitrogen having two starred wavy bonds in formula (13) is a portion of a different hemiaminal group.

More specific divalent bridging groups have the formula (14):

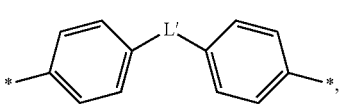

(13)

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. In an embodiment, R' and R" are independently selected from the group consisting of methyl, ethyl, propyl, isopropyl, phenyl, and combinations thereof. Other L' groups include methylene (*—CH$_2$—*), isopropylidenyl (*—C(Me)$_2$-*), and fluorenylidenyl:

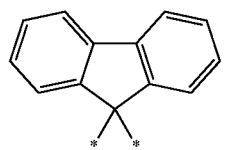

Polyhemiaminals composed of divalent bridging groups of formula (14) can be represented herein by formula (15):

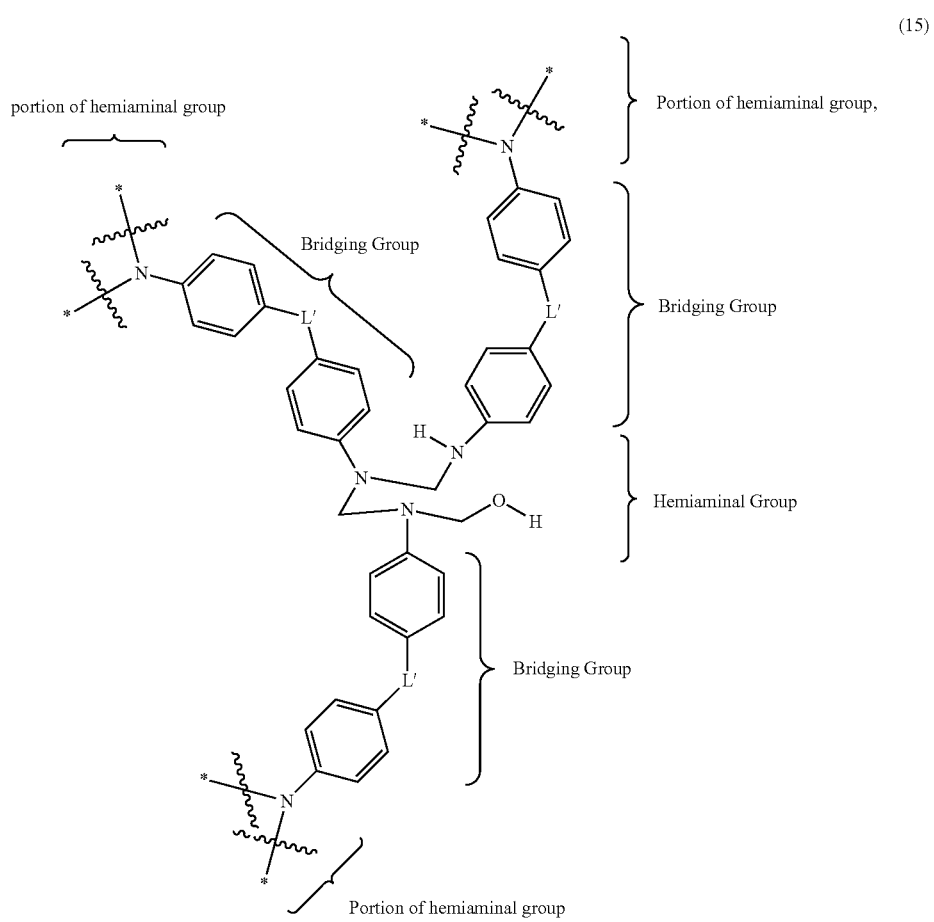

(15)

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (15) is a portion of a different hemiaminal group.

The polyhemiaminal of formula (15) can also be represented by the notation of formula (16):

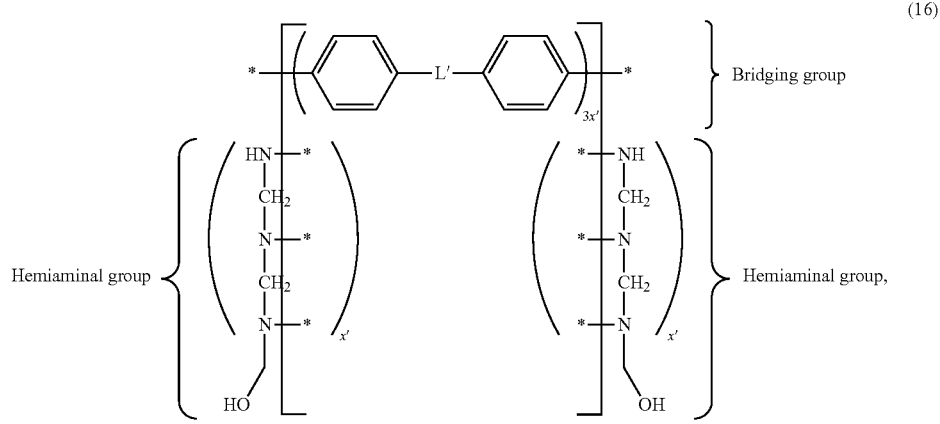

wherein x' is moles, and L' is a divalent linking group selected from the group consisting of *—O—*, *—S—*, *—N(R')—*, *—N(H)—*, *—R"—*, and combinations thereof, wherein R' and R" independently comprise at least 1 carbon. Each starred nitrogen bond of a given hemiaminal group of formula (16) is covalently linked to a respective one of the bridging groups. Additionally, each starred bond of a given bridging group of formula (16) is covalently linked to a respective one of the hemiaminal groups.

The hemiaminal groups can be bound non-covalently to water and/or a solvent. A non-limiting example is a hemiaminal group that is hydrogen bonded to two water molecules as shown in formula (17):

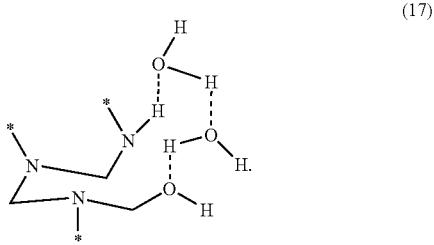

In some embodiments, a hemiaminal material may form a covalent network with water molecules that may be a polyhemiaminal hydrate (PHH). A PHA material of this form may be made, for example, by reaction of polyethylene glycol oligomers with paraformaldehyde. Such materials may be organogels in some cases.

Typical HT and HA polymers and oligomers, and PHH materials, as described herein may be disassembled in aqueous solutions. HT oligomers and polymers will disassemble into monomers and may dissolve in acid solutions having pH less than about 3, such as less than about 2.5, for example less than about 2. PHH materials may disassemble into monomers in neutral water. Such properties may be useful in removing antimicrobial material from a substrate. If an antimicrobial coating on a substrate becomes compromised or otherwise exhibits a reduced antimicrobial or anti-fouling functionality, and it is desirable to re-use the substrate, the HT and HA materials of the antimicrobial material may be removed from the substrate. Thus, the substrate may be re-utilized and re-coated with the antimicrobial material, if desired.

An HA material suitable for use according to the methods described herein may be made using the same groups of reactants as for the HT materials. The diluent monomers described above may also be used to make HA materials. A method of preparing a polyhemiaminal (PHA) comprising divalent bridging groups comprises forming a first mixture comprising i) a monomer comprising two or more primary aromatic amine groups, ii) an optional diluent monomer comprising one aromatic primary amine group, iii) paraformaldehyde, and iv) a solvent. The first mixture is then preferably heated at a temperature of about 20° C. to about 120° C. for about 1 minute to about 24 hours, thereby forming a second mixture comprising the PHA. In an embodiment, the monomer comprises two primary aromatic amine groups. The mole ratio of paraformaldehyde: total moles of primary aromatic amine groups (e.g., diamine monomer plus optional monoamine monomer) may be about 1:1 to about 1.25:1, based on one mole or equivalent of paraformaldehyde equal to 30 grams. The solvent can be any suitable solvent. Exemplary solvents include dipolar aprotic solvents such as, for example, N-methyl-2-pyrrolidone (NMP), dimethylsulfoxide (DMSO), N,N-dimethylformamide (DMF), N,N-dimethylacetamide (DMA), Propylene carbonate (PC), N-cyclohexyl-2-pyrrolidone (CHP), N,N'-dimethylpropyleneurea (DMPU), and propylene glycol methyl ether acetate (PGMEA).

A PHT material may be prepared from a PHA material. The PHT can be prepared by heating a solution comprising the PHA at a temperature of at least 50° C., such as about 165° C. to about 280° C. or about 180° C. to about 220° C., for example at about 200° C. for about 1 minute to about 24 hours. Additionally, a mixed PHA/PHT copolymer may be made by partially converting a PHA material to a PHT material. A combination of low conversion temperature, for example about 150° C. to about 165° C., and short conversion time, for example about 1 minute to about 10 minutes, may be used to make a mixed PHA/PHT material.

An exemplary PHA material may be made by reaction of 4,4'-oxydianiline (ODA) with paraformaldehyde (PF). The product is a powder or solid plastic.

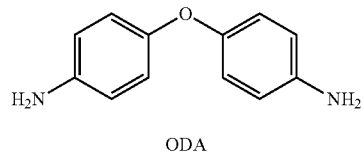 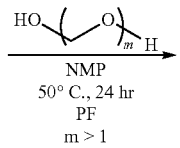

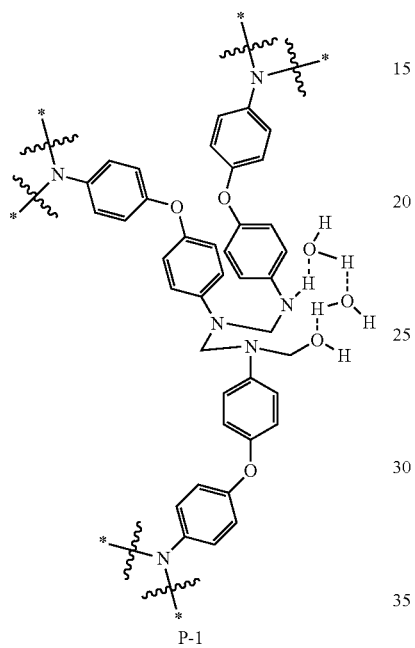

4,4'-Oxydianiline (ODA, 0.20 g, 1.0 mmol) and paraformaldehyde (PF, 0.15 g, 5.0 mmol, 5 equivalents (eq.)) were weighed out into a 2-Dram vial inside a $N_2$-filled glovebox. N-methylpyrrolidone (NMP, 6.2 g, 6.0 mL, 0.17 M) was added. The vial was capped but not sealed. The reaction mixture was removed from the glovebox, and heated in an oil bath at 50° C. for 24 hours (after approximately 0.75 hours, the polymer begins to precipitate). The polyhemiaminal P-1 was precipitated in acetone or water, filtered and collected to yield 0.22 g, >98% yield as a white solid.

A second exemplary PHA material may be prepared by reaction of 4,4'-methylenedianiline (MDA) with PF:

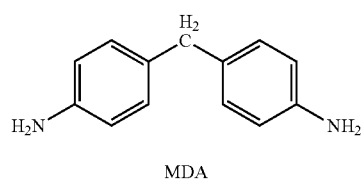 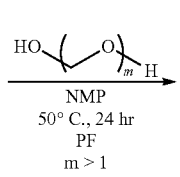

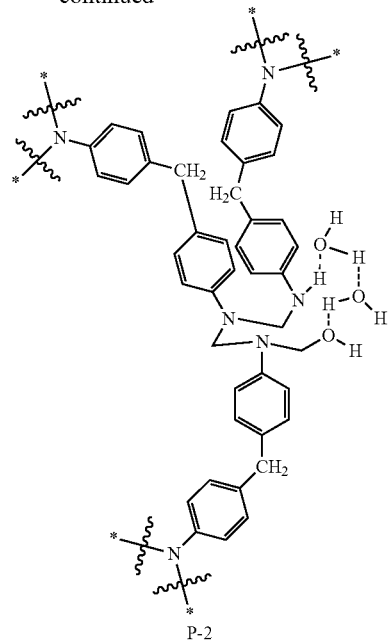

ODA was substituted with 4,4'-methylenedianiline (MDA) and a mole ratio of MDA to PF of 1:5 was used. Solid yield of 0.15 g, 69%, was an amorphous, insoluble off-white powder.

A PHT material may be prepared by reaction of ODA and PF, as follows:

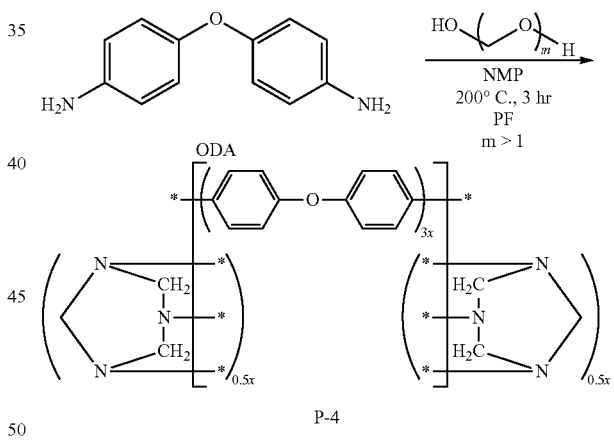

P-4, a polyhexahydrotriazine, was prepared by reaction of 4,4'-oxydianiline (ODA) with paraformaldehyde (PF). ODA (0.20 g, 1.0 mmol) and PF (0.15 g, 5.0 mmol, 2.5 eq.) were weighed out into a 2-Dram vial inside a $N_2$-filled glovebox. NMP (6.2 g, 6.0 mL, 0.17 M) was added. The reaction mixture was removed from the glovebox, and heated in an oil bath at 200° C. for 3 hours (after approximately 0.25 hours, the polymer begins to gel in the NMP). The solution was allowed to cool to room temperature and the polymer was precipitated in 40 mL of acetone, allowed to soak for 12 hours, then filtered and dried in a vacuum oven overnight and collected to yield 0.21 g, 95% yield of P-4 as an off-white solid.

The antimicrobial materials and antimicrobial material precursors described herein may be included in a composite material that may be used as an antimicrobial material in any of the embodiments described herein. Any desired blend material for a composite may be added to the reaction mixture of diamine and aldehyde prior to formation of a reaction product. For example, reactants may be mixed at a non-reacting temperature, for example less than about 50° C. for some embodiments, and a solid polymer material, for example a powder, a fiber aggregate, or a nanotube aggregate, may be added. The resulting combination may be mixed as the temperature is increased to form a reaction product. Any desired polymer may form a composite material with an HA, HT, or PHH material to provide selected properties. Carbon nanotubes may also form a composite with HA, HT, or PHH materials to provide additional mechanical integrity in certain antimicrobial material applications.

While the foregoing is directed to example embodiments of the present disclosure, other and further embodiments may be devised without departing from the basic scope thereof, and the scope thereof is determined by the claims that follow.

What is claimed is:

1. A method comprising:
    preparing an antimicrobial material precursor comprising an anti-fouling material and an adhesive agent, wherein the antimicrobial material precursor is a polyhexahydrotriazine material;
    disposing the antimicrobial material precursor on a substrate; and
    exposing the antimicrobial material precursor to metal ions to form an antimicrobial material.

2. The method of claim 1, wherein the antimicrobial material precursor is a reaction product of a formaldehyde and a primary diamine.

3. The method of claim 1, wherein the polyhexahydrotriazine material comprises an aromatic bridging group.

4. The method of claim 2, wherein the antimicrobial material precursor is a material comprising the polyhexahydrotriazine material and a polyhemiaminal material.

5. The method of claim 1, wherein the anti-fouling material comprises polyethylene glycol.

6. The method of claim 1, wherein the adhesive agent comprises dopamine.

7. The method of claim 1, wherein the metal ions are dissolved in a polar solvent.

8. The method of claim 1, wherein the metal ions comprise silver ions and/or copper ions.

9. The method of claim 1, wherein the antimicrobial material precursor is formed by a process comprising:
    forming a mixture comprising one or more monomers comprising two aromatic primary amine groups having the general structure H$_2$N—Ar-L'-Ar-N—H$_2$, wherein Ar denotes a benzene ring group and L' is a divalent linking group, and a solvent; and
    heating the mixture at a temperature of about 50° C. to about 280° C. for about 1 minute to about 24 hours.

10. A method, comprising:
    preparing an antimicrobial material precursor comprising an anti-fouling material, wherein the antimicrobial material precursor is a polyhexahydrotriazine material;
    disposing an adhesive agent layer on the surface of a substrate;
    disposing the antimicrobial material precursor on the adhesive agent layer; and
    exposing the antimicrobial material precursor to metal ions to form an antimicrobial material.

11. The method of claim 10, wherein the antimicrobial material precursor is a reaction product of an aldehyde and a primary diamine.

12. The method of claim 10, wherein the polyhexahydrotriazine material comprises an aromatic bridging group.

13. The method of claim 12, wherein the polyhexahydrotriazine material has a plurality of trivalent hexahydrotriazine groups having the structure

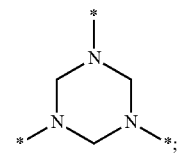

and
a plurality of divalent bridging groups having the structure

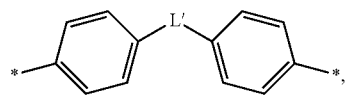

each divalent bridging group bonded to two of the trivalent hexahydrotriazine groups, wherein L' is a divalent linking group.

14. The method of claim 10, wherein the antimicrobial material precursor comprises a hexahydrotriazine material having a plurality of trivalent hexahydrotriazine groups having the structure

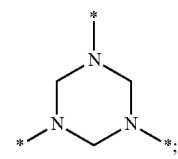

and
a plurality of divalent bridging groups having the structure

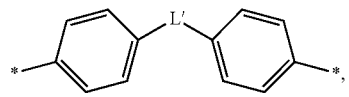

each divalent bridging group bonded to two of the trivalent hexahydrotriazine groups, wherein L' is a divalent linking group.

15. The method of claim 10, wherein the adhesive agent a monomer that is homopolymerized onto the surface of the substrate.

16. The method of claim 15, wherein the monomer comprises dopamine.

17. The method of claim 10, wherein the metal ions comprise silver ions and/or copper ions.

18. A method comprising:
    preparing an antimicrobial material precursor comprising an anti-fouling material, wherein the antimicrobial material precursor comprises a hexahydrotriazine material having a plurality of trivalent hexahydrotriazine groups having the structure

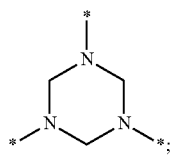

and
a plurality of divalent bridging groups having the structure

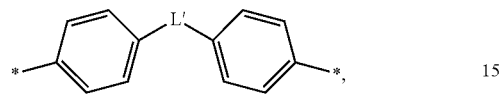

each divalent bridging group bonded to two of the trivalent hexahydrotriazine groups, wherein L' is a divalent linking group an anti-fouling material;
  disposing the antimicrobial material precursor on a surface of a substrate substrate; and
  exposing the antimicrobial material precursor to silver and/or copper ions to form an antimicrobial material.

* * * * *